US00PP09897P

United States Patent [19]

Perry

[11] Patent Number: Plant 9,897

[45] Date of Patent: May 20, 1997

[54] OSTEOSPERMUM PLANT NAMED 'STARDUST'

[76] Inventor: Patricia G. Perry, River Gardens Sleights, Whitby North Yorkshire, England, YO21 1RR

[21] Appl. No.: 582,692

[22] Filed: Jan. 3, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—C. A. Whealy

[57] ABSTRACT

A new and distinct cultivar of *Osteospermum jucundum* named Stardust, characterized by its compact and dense plant habit; broad and glossy foliage; intense purple flower color; strong peduncles and upright, erect flowers; and very long flowering period.

1 Drawing Sheet

The present invention relates to a new and distinct cultivar of Osteospermum plant, botanically known as *Osteospermum jucundum* and referred to by the cultivar name Stardust.

The new cultivar was selected by the inventor from seedling progeny from a cross of unknown parents of *Osteospermum jucundum* by the inventor at her garden in North Yorkshire, England, with the intent of selecting an improvement of the nonpatented *Osteopermum jucundum* cultivar Ralph Gould.

Asexual reproduction of the new cultivar by terminal cuttings taken in Sussex and Worcestershire, England, has shown that the unique features of this new Osteospermum are stabilized and are reproduced true to type in successive propagations.

The new cultivar has not been observed under all possible environmental conditions. The phenotype may vary somewhat with variations in environment such as temperature, daylength and light intensity, without, however, any variance in genotype. The following observations, measurments, values, and comparisons describe plants grown in Sussex, England, under outdoor conditions which closely approximate those generally used in commercial horticulture and garden practice.

The following characteristics have been repeatedly observed and are determined to be basic characteristics of Stardust, which in combination distinguish this Osteospermum from other Osteospermums, specifically the cultivar Ralph Gould, and distinguish Stardust as a new and distinct cultivar:

1. Compact and dense plant habit. Plants of Stardust are generally more compact, denser and less spreading than other *Osteospermum jucundum* types such as the cultivar Ralph Gould.

2. Broad and glossy foliage. Leaves of plants of Stardust are broader and more glossy than other *Osteospermum jucundum* types such as the cultivar Ralph Gould.

3. Intense purple flower color. Flowers of plants of Stardust have a more intense purple flower color compared with other *Osteospermum jucundum* types such as the cultivar Ralph Gould.

4. Strong peduncles and upright, erect flowers. Plants of Stardust have strong peduncles that support flowers in a more erect position than other *Osteospermum jucundum* types such as the cultivar Ralph Gould.

5. Very long flowering period. Plants of Stardust flower for a longer period of time than other *Osteospermum jucundum* types such as the cultivar Ralph Gould.

A detailed comparison of the differences between the cultivars Stardust and Ralph Gould appears in Chart A at the end of the specification.

The accompanying colored photograph illustrates the overall appearance of the new cultivar, showing the colors as true as it is reasonably possible to obtain in colored reproductions of the type. The photograph comprises a top perspective view of a single potted plant of Stardust. Flower color in the photograph appears lighter than the actual flower color due to light reflectance.

The following description of the new culitvar is based on plants produced in Sussex, England, under outdoor conditions in summer with average day temperatures ranging from 15 to 25°C. and average night temperatures ranging from 8 to 15°C. Color references are made to The Royal Horticultural Society Colour Chart except where general terms of ordinary dictionary significance are used.

Botanical classification: *Osteospermum jucundum* cultivar Stardust.

Parentage: Unidentified varieties of *Osteospermum jucundum.*

Progagation:

*Type.*—By cuttings.

*Time to initiate roots.*—Summer: 10 days at temperatures of 20 to 25°C. Winter: 15 days at temperatures of 15 to 20°C.

*Rooting habit.*—Fibrous and branching.

Plant description:

*General appearance.*—Rounded low growing (20 to 45 cm) plant with dense foliage and erect flower stems. Freely branching and growth rate is moderate. Appropriate for 1 to 2–liter containers. To produce a 1.5–liter plant from unrooted cuttings, it takes 3 months under summer conditions and 4 months under winter conditions.

*Foliage description.*—Arrangement: Alternate, single. Leaf shape: Lanceolate Leaf margin: Widely-spaced blunt teeth. Leaf apex: Rounded or with a small point. Leaf base: Attenuate. Leaf aspect: Flat. Leaf length: 5 to 15 cm. Leaf width: 1.5 to 4 cm. Leaf texture: Top and under sides glossy, slightly pubescent. Leaf attachment: Sessile, leaf base attenuated. Venation pattern: Palmate. Fragrance: Strongly fragrant. Leaf color: Young leaves: Top side: 146A. Under side: 146B. Fully expanded leaves: Top side: 137A. Under side: 137C. Attenuated leaf base: 139D. Venation: Top side: 139D. Under side: 144B.

Flowering description:

*Inflorescence.*—Daisy–type composite inflorescence form. Flowers arranged acropetally on a capitulum.

Inflorescences are long-lasting on the plant and as cut flowers. Inflorescences persistent.

*Natural flowering season.*—Natural flowering season is April to October in the northern hemishpere. Plants flower continuously during this period.

*Quantity of inflorescences.*—Abundant from April to October.

*Inflorescence diameter.*—5.5 to 8 cm.

*Inflorescence depth (height).*—2.5 to 4 cm.

*Fragrance.*—Not detectable.

*Ray florets.*—Appearance: Satiny. Texture: Smooth and slightly glossy. Shape: Lanceolate. Margin: Entire. Tip: Rounded or sometimes emarginate with 3 lobes. Length: 2.5 to 4 cm. Width: 6 to 10 mm. Color: When opening, upper side: 80B. Mature, top side: 78A. Mature, under side: 186C with darker stripes. Fading to: 78C. Number of ray florets per inflorescence: 12 to 20.

*Disc florets.*—Shape: Tubular, slightly funnel-shaped. Diameter of disc: 10 to 15 mm. Length: 5 to 10 mm. Width: 1 mm widening to a 5-petal corolla 2 mm in diameter. Color: Immature: 188A. Mature: 164B. Number of disc florets per inflorescence: Numerous.

*Peduncle.*—Length: 10 to 20 cm. Strength: Strong, inflorescences held erect above foliage. Color: 146D with 59B. Texture: Rough.

*Flower bud.*—Shape: Pointed. Length: 10 to 25 mm. Diameter: 10 to 15 mm. Color: 93A with 138A.

*Sepals.*—Arrangement: Appressed to ray florets. Shape: Narrowly lanceolate with pointed tip. Quantity: 15 to 25. Texture: Rough with short coarse short hairs. Color, under side: 146B.

Disease resistance: No susceptibility nor resistance to fungal, bacterial or viral pathogens has been noted.

Seed production: Seed production is occasionally observed.

CHART A

| CHARACTERISTIC | 'STARDUST' | 'RALPH GOULD' |
|---|---|---|
| PLANT SHAPE | Compact | Somewhat spreading |
| GROWTH HABIT | Dense | Moderately dense, more open |
| QUANTITY OF LEAVES PER SHOOT | 5 to 20 | 10 to 30 |
| LEAF SHAPE | Lanceolate | Linear-lanceolate, more narrow |
| LEAF WIDTH | 15 to 35 mm | 5 to 25 mm |
| LEAF TEXTURE | Glossy | Dull |
| VENATION | Mid-rib slightly sunken below upper surface | Mid-rib protrudes above upper surface |
| RAY FLORET COLOR, MATURE TOP SIDE | 78A | 75A |
| RAY FLORET COLOR, MATURE UNDER SIDE | 186C with darker stripes | 165C |
| RAY FLORET COLOR, FADING TO | 78C | 75A |
| QUANTITY OF RAY FLORETS | 12 to 20 | 15 to 25 |
| DISC FLORET COLOR, IMMATURE | 188A | 116A |
| PEDUNCLE STRENGTH | Strong | Moderately strong |
| PEDUNCLE ANGLE | Upright, erect | Less upright, not as erect |

It is claimed:

1. A new and distinct cultivar of *Osteospermum jucundum* named Stardust, as illustrated and described.

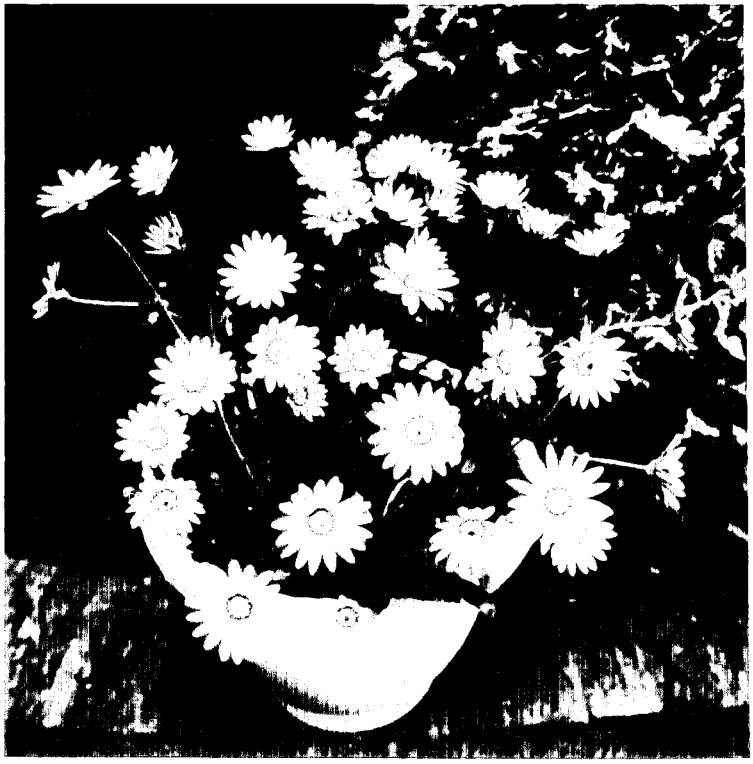

* * * * *